(12) United States Patent
Richard et al.

(10) Patent No.: US 9,808,245 B2
(45) Date of Patent: Nov. 7, 2017

(54) COUPLING ASSEMBLY FOR INTERCONNECTING AN ADAPTER ASSEMBLY AND A SURGICAL DEVICE, AND SURGICAL SYSTEMS THEREOF

(71) Applicant: Covidien LP, Mansfield, MA (US)

(72) Inventors: Paul Richard, Shelton, CT (US); Joseph Pierre, Bulbston Lake, NY (US)

(73) Assignee: Covidien LP, Mansfield, MA (US)

( * ) Notice: Subject to any disclaimer, the term of this patent is extended or adjusted under 35 U.S.C. 154(b) by 422 days.

(21) Appl. No.: 14/515,030

(22) Filed: Oct. 15, 2014

(65) Prior Publication Data

US 2015/0164502 A1    Jun. 18, 2015

Related U.S. Application Data

(60) Provisional application No. 61/915,667, filed on Dec. 13, 2013.

(51) Int. Cl.
*A61B 17/068* (2006.01)
*A61B 17/00* (2006.01)
(Continued)

(52) U.S. Cl.
CPC ...... *A61B 17/068* (2013.01); *A61B 17/00234* (2013.01); *A61B 17/07207* (2013.01);
(Continued)

(58) Field of Classification Search
CPC ............... A61B 2017/07214; A61B 17/068
(Continued)

(56) References Cited

U.S. PATENT DOCUMENTS 2,777,340 A    1/1957    Hettwer et al.
2,957,353 A    10/1960   Babacz
(Continued)

FOREIGN PATENT DOCUMENTS

AU    2008229795 A1    4/2009
CA    2451558 A1    1/2003
(Continued)

OTHER PUBLICATIONS

Extended European Search Report corresponding to International Application No. EP 15 15 1076.5 dated Apr. 22, 2015.
(Continued)

*Primary Examiner* — Gloria R Weeks

(57) ABSTRACT

A coupling assembly selectively interconnects a surgical device with an adapter assembly. The adapter assembly is configured for connection with a surgical attachment. The coupling assembly includes a first connector, a second connector and an outer tube. The first connector is configured for mating engagement with a surgical device. The second connector is configured for mating engagement with an adapter assembly. The outer tube extends between and has a first end and a second end defining a longitudinal axis therebetween. The first end of the outer tube supports the first connector. The second end of the outer tube supports the second connector. The longitudinal axis of the outer tube extends transversely relative to a longitudinal axis defined by a surgical device.

20 Claims, 6 Drawing Sheets

(51) Int. Cl.
*A61B 17/072* (2006.01)
*A61B 17/115* (2006.01)
*A61B 17/29* (2006.01)

(52) U.S. Cl.
CPC . *A61B 17/1155* (2013.01); *A61B 2017/00017* (2013.01); *A61B 2017/0046* (2013.01); *A61B 2017/00398* (2013.01); *A61B 2017/00464* (2013.01); *A61B 2017/00477* (2013.01); *A61B 2017/00734* (2013.01); *A61B 2017/2903* (2013.01); *A61B 2017/2923* (2013.01); *Y10T 29/49002* (2015.01); *Y10T 74/1913* (2015.01)

(58) Field of Classification Search
USPC ..................................................... 227/181.1
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,869,719 A | 9/1989 | Hogan |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,289,963 A * | 3/1994 | McGarry ........... A61B 17/0684 227/175.1 |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,575,799 A * | 11/1996 | Bolanos ............. A61B 17/0684 227/175.1 |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,968,012 A | 10/1999 | Ren et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,197,002 B1 | 3/2001 | Peterson |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,692,482 B2 | 2/2004 | Heller et al. |
| 6,698,643 B2 | 3/2004 | Whitman |
| 6,699,177 B1 | 3/2004 | Laby et al. |
| 6,706,018 B2 | 3/2004 | Westlund et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,094,220 B2 | 8/2006 | Tanghoj et al. |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |

(56) References Cited

U.S. PATENT DOCUMENTS

| | | |
|---|---|---|
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,731,707 B2 | 6/2010 | Heller et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,798,999 B2 | 9/2010 | Bailey et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,854,727 B2 | 12/2010 | Belsley |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,988,699 B2 | 8/2011 | Martz et al. |
| 7,992,758 B2 | 8/2011 | Whitman et al. |
| 8,016,178 B2 | 9/2011 | Olson et al. |
| 8,016,752 B2 | 9/2011 | Armstrong et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,025,621 B2 | 9/2011 | Ewaschuk et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,292,963 B2 | 10/2012 | Miller et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,444,625 B2 | 5/2013 | Stalker et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0128607 A1 | 9/2002 | Haury et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2004/0260246 A1 | 12/2004 | Desmond |
| 2005/0004553 A1 | 1/2005 | Douk |
| 2005/0075711 A1 | 4/2005 | Neary |
| 2005/0096507 A1 | 5/2005 | Prosek |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0200185 A1 | 9/2006 | Marchek et al. |
| 2006/0229573 A1 | 10/2006 | Lamborne |

(56) References Cited

U.S. PATENT DOCUMENTS

| | | |
|---|---|---|
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228233 A1 | 9/2010 | Kahn |
| 2011/0071508 A1 | 3/2011 | Duval et al. |
| 2011/0077673 A1 | 3/2011 | Grubac et al. |
| 2011/0118577 A1 | 5/2011 | Pfeiffer et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016402 A1 | 1/2012 | Weisshaupt et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116248 A1 | 5/2012 | McWeeney et al. |
| 2012/0116368 A1 | 5/2012 | Viola |
| 2012/0123389 A1 | 5/2012 | Shafran |
| 2012/0143002 A1 | 6/2012 | Aranyi et al. |
| 2012/0150063 A1 | 6/2012 | Rea |
| 2012/0172924 A1 | 7/2012 | Allen, IV |
| 2012/0223121 A1 | 9/2012 | Viola et al. |
| 2012/0245426 A1 | 9/2012 | Salvas et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323081 A1 | 12/2012 | Son |
| 2012/0323226 A1 | 12/2012 | Chowaniec et al. |
| 2012/0330285 A1 | 12/2012 | Hartoumbekis et al. |
| 2013/0012983 A1 | 1/2013 | Kleyman |
| 2013/0018361 A1 | 1/2013 | Bryant |
| 2013/0053782 A1 | 2/2013 | Shelton, IV |
| 2013/0090531 A1 | 4/2013 | Ryan |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0110085 A1 | 5/2013 | Adamson |
| 2013/0165942 A1 | 6/2013 | Tan-Malecki et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0220345 A1 | 8/2013 | Allphin et al. |
| 2013/0237950 A1 | 9/2013 | Gianotti et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |

(56) References Cited

FOREIGN PATENT DOCUMENTS

| | | |
|---|---|---|
| EP | 1 813 203 A2 | 8/2007 |
| EP | 1813199 A1 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| ES | 2333509 A1 | 2/2010 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 00/72760 A1 | 12/2000 |
| WO | 00/72765 A1 | 12/2000 |
| WO | 03/000138 A2 | 1/2003 |
| WO | 03/026511 A1 | 4/2003 |
| WO | 03/030743 A2 | 4/2003 |
| WO | 03065916 A1 | 8/2003 |
| WO | 03/077769 A1 | 9/2003 |
| WO | 03090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/073577 A2 | 6/2009 |
| WO | 2009/132359 A2 | 10/2009 |
| WO | 2009/143092 A1 | 11/2009 |
| WO | 2009149234 A1 | 12/2009 |
| WO | 2010030114 A2 | 3/2010 |
| WO | 2011/108840 A2 | 9/2011 |
| WO | 2012040984 A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report dated Aug. 5, 2015, corresponding to European Patent Application No. 14197563.1; 14 pages.
Partial European Search Report, dated Apr. 23, 2015, corresponding to European Patent Application No. 14197563.1; 7 pages.
European Communication dated Jan. 31, 2017, corresponding to European Application No. 14 197 563.1; 3 pages.

* cited by examiner

COUPLING ASSEMBLY FOR INTERCONNECTING AN ADAPTER ASSEMBLY AND A SURGICAL DEVICE, AND SURGICAL SYSTEMS THEREOF

CROSS-REFERENCE TO RELATED APPLICATIONS

This application claims the benefit of and priority to U.S. Provisional Patent Application No. 61/915,667, filed Dec. 13, 2013, the entire disclosure of which is incorporated by reference herein.

BACKGROUND

1. Technical Field

The present disclosure relates to coupling assemblies for use in surgical systems. More specifically, the present disclosure relates to coupling assemblies for electrically and mechanically interconnecting electromechanical surgical devices with an adapter assembly, which in turn is connected with a surgical attachment, such as, for example, a surgical loading unit. Surgical systems including hand held electromechanical surgical devices and coupling assemblies for reducing a total length of the surgical system and/or shifting a center of gravity of the surgical system proximally to a user are also provided.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical attachments, such as, for example, surgical loading units, to establish a mechanical and/or electrical connection therebetween. Presently, however, such surgical systems utilizing an adapter assembly are undesirably long, which can be problematic and/or inconvenient for particular surgical applications. For example, the center of gravity of the surgical system shifts further away from a practitioner's hand (i.e., distally) as the surgical system increases in length, thus leading to practitioner fatigue during use.

Accordingly, a need exists for a surgical system including a surgical device, an adapter assembly and a surgical attachment, wherein the surgical system has a reduced length as compared to that which is previously provided by the prior art.

SUMMARY

The present disclosure relates to coupling assemblies for electrical and mechanical interconnection between electromechanical surgical devices and surgical attachments. The present disclosure further relates to surgical systems including a hand held electromechanical surgical device, an adapter assembly, a surgical attachment and a coupling assembly disposed between the adapter assembly and the surgical device to reduce an overall length of the surgical system.

According to an aspect of the present disclosure, a coupling assembly is provided. The coupling assembly selectively interconnects a surgical device with an adapter assembly, which is configured for connection with a surgical attachment. The surgical device defines a longitudinal axis. The coupling assembly comprises a first connector, a second connector and an outer tube. The first connector is configured for mating engagement with the surgical device. The second connector is configured for mating engagement with the adapter assembly. The outer tube extends between and has a first end and a second end defining a longitudinal axis therebetween. The first end of the outer tube supports the first connector and the second end of the outer tube supports the second connector. The longitudinal axis of the outer tube extends transversely relative to the longitudinal axis of the surgical device.

In aspects of the present disclosure, the first connector may be disposed distally of the second connector when the first connector is connected to the surgical device.

It is contemplated that the outer tube may extend transversely relative to the first and second connectors.

In aspects of the present disclosure, the coupling assembly may further comprise at least one rotatable drive shaft disposed within the outer tube.

In some embodiments, the at least one rotatable drive shaft of the coupling assembly may support a first bevel gear and a second bevel gear. The first bevel gear may be disposed adjacent the first connector and may be configured for connection with at least one rotatable drive shaft of the surgical device. The second bevel gear may be disposed adjacent the second connector and may be configured for connection with at least one rotatable drive shaft of the adapter assembly. A rotation of the at least one rotatable drive shaft of the surgical device may result in a rotation of the at least one rotatable drive shaft of the adapter assembly via the at least one rotatable drive shaft of the coupling assembly.

It is envisioned that each of the first and second connectors may include at least one gear shaft. The at least one gear shaft of the first connector may be connectible between the at least one drive shaft of the surgical device and the first bevel gear. The at least one gear shaft of the second connector may be connectible between the at least one drive shaft of the adapter assembly and the second bevel gear.

In another embodiment, the first and second connectors may each include an inner surface defining a cavity in communication with a passageway extending through a length of the outer tube.

In embodiments, the outer tube may extend at an angle less than 90 degrees relative to the longitudinal axis of the surgical device.

In another aspect of the present disclosure, an electromechanical surgical system is provided. The electromechanical surgical system comprises a hand-held electromechanical surgical device configured to actuate a surgical attachment that is configured to perform at least one function. The surgical device includes a housing and at least one rotatable drive shaft disposed within the housing for driving actuation of the surgical attachment. The at least one rotatable drive shaft of the surgical device defines a longitudinal axis.

The surgical system further comprises an adapter assembly for selective interconnection between the surgical device and the surgical attachment. The adapter assembly includes at least one rotatable drive shaft and is configured to convert a rotational force of the at least one rotatable drive shaft of the surgical device into an axial force for actuating the surgical attachment.

The surgical system further comprises a coupling assembly for coupling the surgical device and the adapter assembly. The coupling assembly includes a first connector configured for mating engagement with the surgical device. A second connector of the coupling assembly is configured for mating engagement with the adapter assembly. An outer tube of the coupling assembly extends between and has a first end and a second end defining a longitudinal axis therebetween. The first end of the outer tube supports the first connector and the second end of the outer tube supports the second connector. The longitudinal axis of the coupling assembly extends transversely relative to the longitudinal axis of the surgical device.

In aspects of the present disclosure, the first connector may be disposed distally of the second connector when the first connector is connected to the surgical device.

It is contemplated that the outer tube may extend transversely relative to the first and second connectors.

In some embodiments, the coupling assembly may further comprise at least one rotatable drive shaft disposed within the outer tube and may be connectible with the at least one rotatable drive shaft of the surgical device and the at least one rotatable drive shaft of the adapter assembly.

It is envisioned that the at least one rotatable drive shaft of the coupling assembly may support a first bevel gear and a second bevel gear. The first bevel gear may be disposed adjacent the first connector and may be configured for connection with the at least one rotatable drive shaft of the surgical device. The second bevel gear may be disposed adjacent the second connector and may be configured for connection with the at least one rotatable drive shaft of the adapter assembly. A rotation of the at least one rotatable drive shaft of the surgical device may result in a rotation of the at least one rotatable drive shaft of the adapter assembly via the at least one rotatable drive shaft of the coupling assembly.

In aspects of the present disclosure, the first and second connectors may each include an inner surface defining a cavity in communication with a passageway extending through a length of the outer tube.

In some embodiments, the outer tube may extend at an angle less than 90 degrees relative to the longitudinal axis of the surgical device.

It is contemplated that the housing may include an upper housing portion. The upper housing portion may extend between and have a proximal end and a distal end. A lower hand grip portion may extend from the proximal end of the upper housing portion.

It is envisioned that the second connector may be disposed proximal to the distal end of the upper housing portion when the first connector of the first connector is matingly engaged with the surgical device.

In aspects of the present disclosure, the coupling assembly may extend at an angle less than 90 degrees relative to the distal end of the upper housing portion when the first connector is matingly engaged with the surgical device.

In yet another aspect of the present disclosure, a method of assembling an electromechanical surgical system is provided. The method comprises providing a surgical attachment configured for performing at least one function; and providing a hand-held electromechanical surgical device configured to actuate the surgical attachment.

The surgical device includes a housing and at least one rotatable drive shaft disposed within the housing. The at least one rotatable drive shaft drives the at least one function of the surgical attachment. The at least one rotatable drive shaft of the surgical device defines a longitudinal axis The method further comprises providing an adapter assembly for selective interconnection between the surgical device and the surgical attachment. The adapter assembly includes at least one rotatable drive shaft. The at least one rotatable drive shaft is configured to convert a rotational force of the at least one rotatable drive shaft of the surgical device into an axial force for actuating the surgical attachment.

The method further comprises providing a coupling assembly for coupling the surgical device and the adapter assembly. The coupling assembly includes: a first connector configured for mating engagement with the surgical device; a second connector configured for mating engagement with the adapter assembly; and an outer tube having a first end and a second end defining a longitudinal axis therebetween. The first end of the outer tube supports the first connector and the second end of the outer tube supports the second connector. The longitudinal axis of the outer tube extends transversely relative to the longitudinal axis of the surgical device.

The method additionally comprises connecting the surgical device with the first connector of the coupling assembly such that the coupling assembly is disposed at an angle less than 90 degrees relative to the surgical device; and connecting the adapter assembly with the second connector of the coupling assembly and the surgical attachment.

In some embodiments, the method may further include connecting the at least one rotatable drive shaft of the surgical device with a first bevel gear of the coupling assembly disposed adjacent the first connector; and connecting the at least one rotatable drive shaft of the adapter assembly with a second bevel gear of the coupling assembly disposed adjacent the second connector. Rotation of the at least one rotatable drive shaft of the surgical device may result in rotation of the at least one rotatable drive shaft of the adapter assembly via the first and second bevel gears of the coupling assembly to actuate the at least one function of the surgical attachment.

As used herein, the terms parallel and perpendicular are understood to include relative configurations that are substantially parallel and substantially perpendicular up to about +/−10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
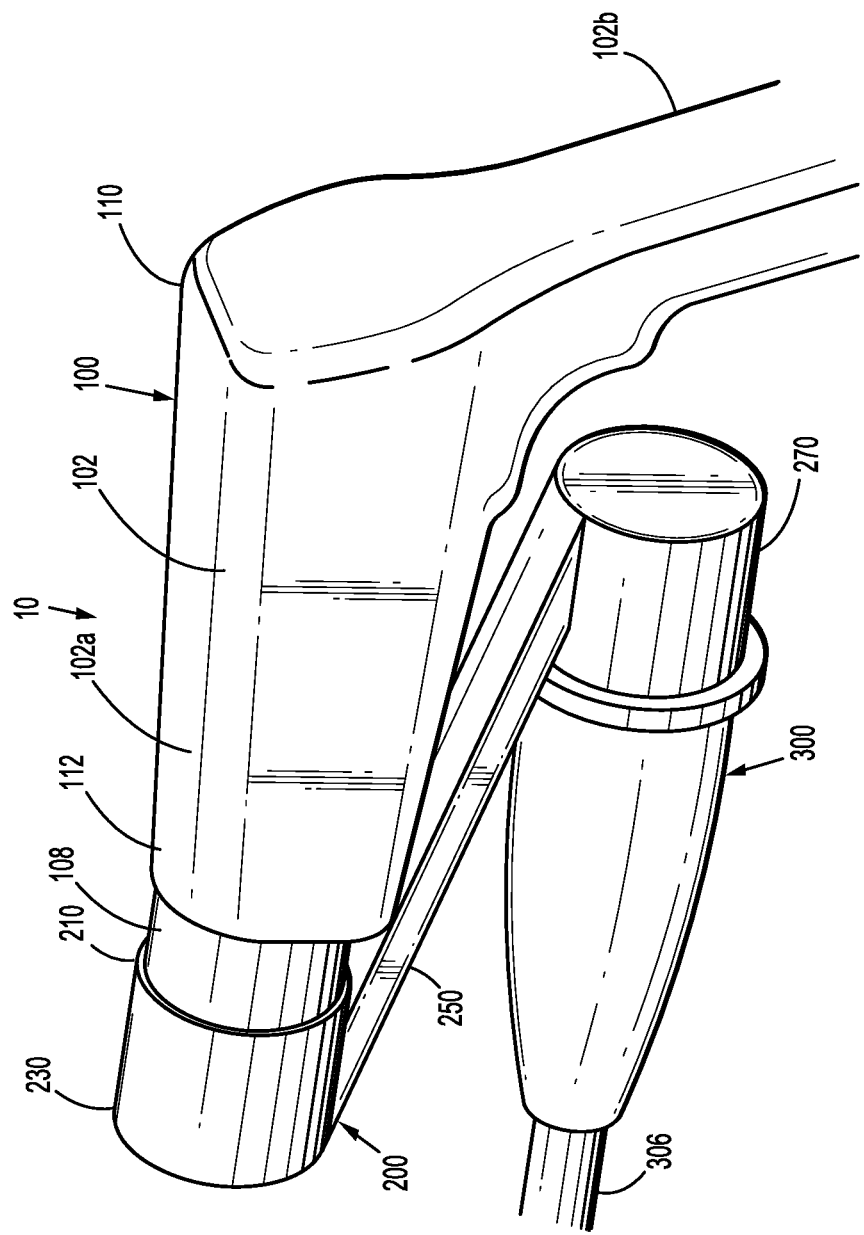
FIG. 1 is a rear, perspective view of an electromechanical surgical system in accordance with an embodiment of the present disclosure.

Embodiments of the presently disclosed surgical devices, coupling assemblies, adapter assemblies, and surgical attachments are described in detail with reference to the drawings, in which like reference numerals designate identical or corresponding elements in each of the several views. As used herein the term "distal" refers to that portion of the surgical device, coupling assembly or adapter assembly, or component thereof, farther from the user. The term "proximal" refers to that portion of the surgical device, coupling assembly or adapter assembly, or component thereof, closer to the user.

With reference to FIGS. 1-4, a surgical device, in accordance with an embodiment of the present disclosure, is generally designated as 100, and is in the form of a powered hand held electromechanical surgical device configured for selective attachment thereto of a plurality of different end effectors, such as, for example, surgical attachments 400 including, but not limited to a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument, each of which being configured for actuation and manipulation by the powered hand held electromechanical surgical device 100.

As illustrated in FIG. 1, a surgical system is provided, such as, for example, an electromechanical surgical system 10. System 10 includes hand-held electromechanical surgical device 100 configured for selective connection with a coupling assembly 200, which is configured for selective connection with an adapter assembly 300, and, in turn, adapter assembly 300 is configured for selective connection with a surgical attachment 400 (e.g., an end effector, multiple-use or single-use loading unit, see FIG. 4) that is configured to perform at least one function. Surgical device 100 is configured and adapted to actuate surgical attachment 400. Coupling assembly 200 is configured such that when engaged between surgical device 100 and adapter assembly 300, coupling assembly 200 reduces an overall length of surgical system 10 as compared to a surgical system without coupling assembly 200 interconnecting surgical device 100 and adapter assembly 300.

Figure 2:
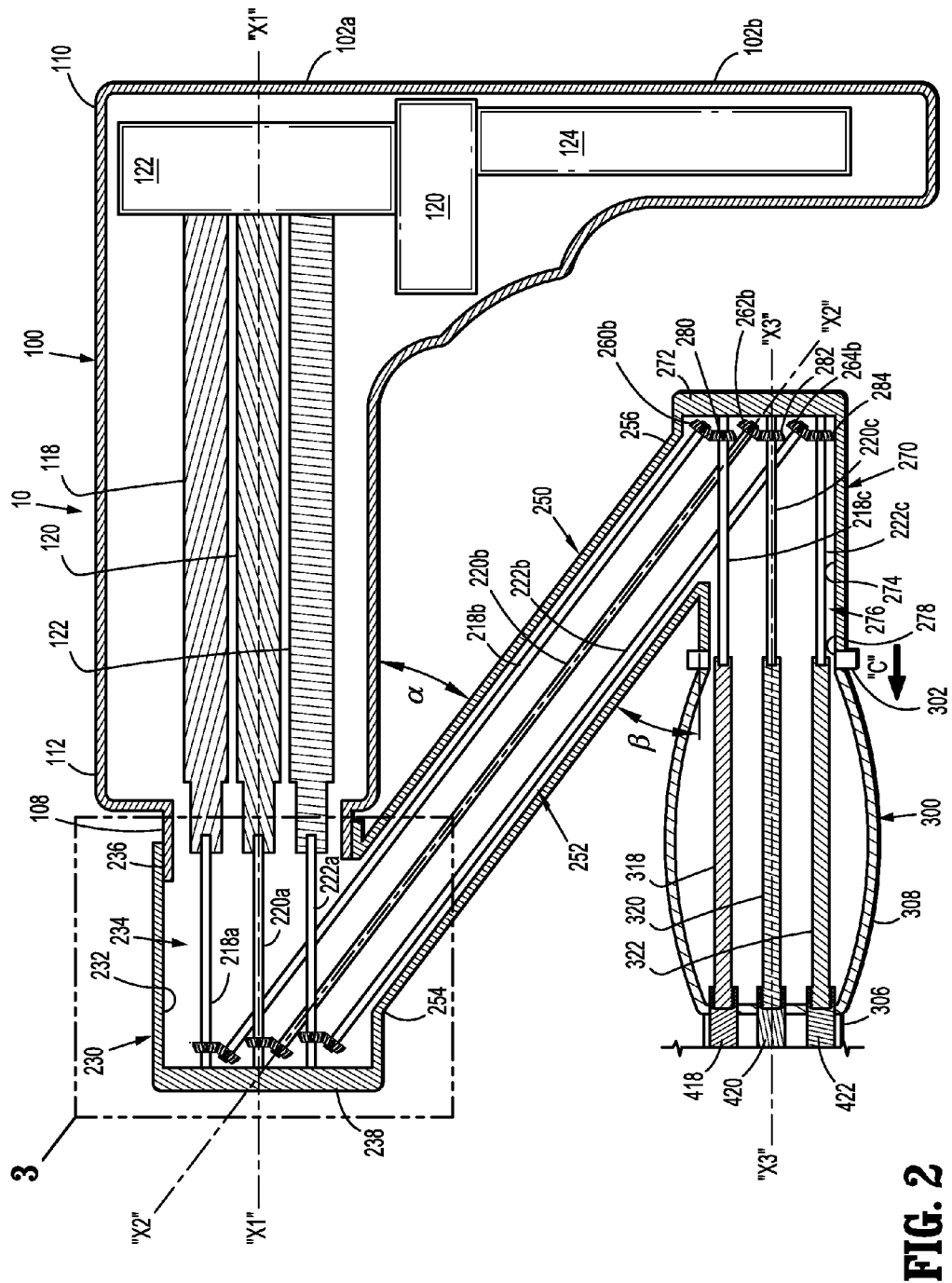
FIG. 2 is a side, cross sectional, schematic view of the system shown in FIG. 1.

As illustrated in FIGS. 1 and 2, surgical device 100 includes a housing, such as, for example, a handle housing 102 including a circuit board 120 and a drive mechanism 122 situated therein. The circuit board 120 is configured to control the various operations of surgical device 100. Handle housing 102 defines a cavity therein for selective removable receipt of a rechargeable battery 124 therein. The battery 124 is configured to supply power to any of the electrical components of surgical device 100 including electric motors used to drive the operation of surgical attachment 400.

As mentioned above, handle housing 102 includes an upper housing portion 102a extending between a proximal end 110 and a distal end 112. Upper housing portion 102a houses various components of surgical device 100. Handle housing 102 further includes a lower hand grip portion 102b extending from upper housing portion 102a. In embodiments, lower hand grip portion 102b may be disposed distally of a proximal-most end of upper housing portion 102a. In some embodiments, lower hand grip portion 102b has various surface features, such as, for example, knurled, smooth, rough, and/or textured to enhance a practitioner's gripping of lower hand grip portion 102b.

Handle housing 102 is configured to house drive mechanism 122 therewithin. Drive mechanism is configured to drive shafts and/or gear components in order to perform the various operations of surgical device 100. In particular, drive mechanism is configured to drive shafts and/or gear components in order to selectively move a tool assembly 404 of surgical attachment 400 (see FIG. 4) relative to a proximal body portion 402 of surgical attachment 400, to rotate surgical attachment 400 about a longitudinal axis relative to handle housing 102, to move/approximate an anvil assembly 406 and a cartridge assembly 408 of surgical attachment 400 relative to one another, and/or to fire a stapling and cutting cartridge within cartridge assembly 408 of surgical attachment 400, as described in further detail herein below.

Figure 3:
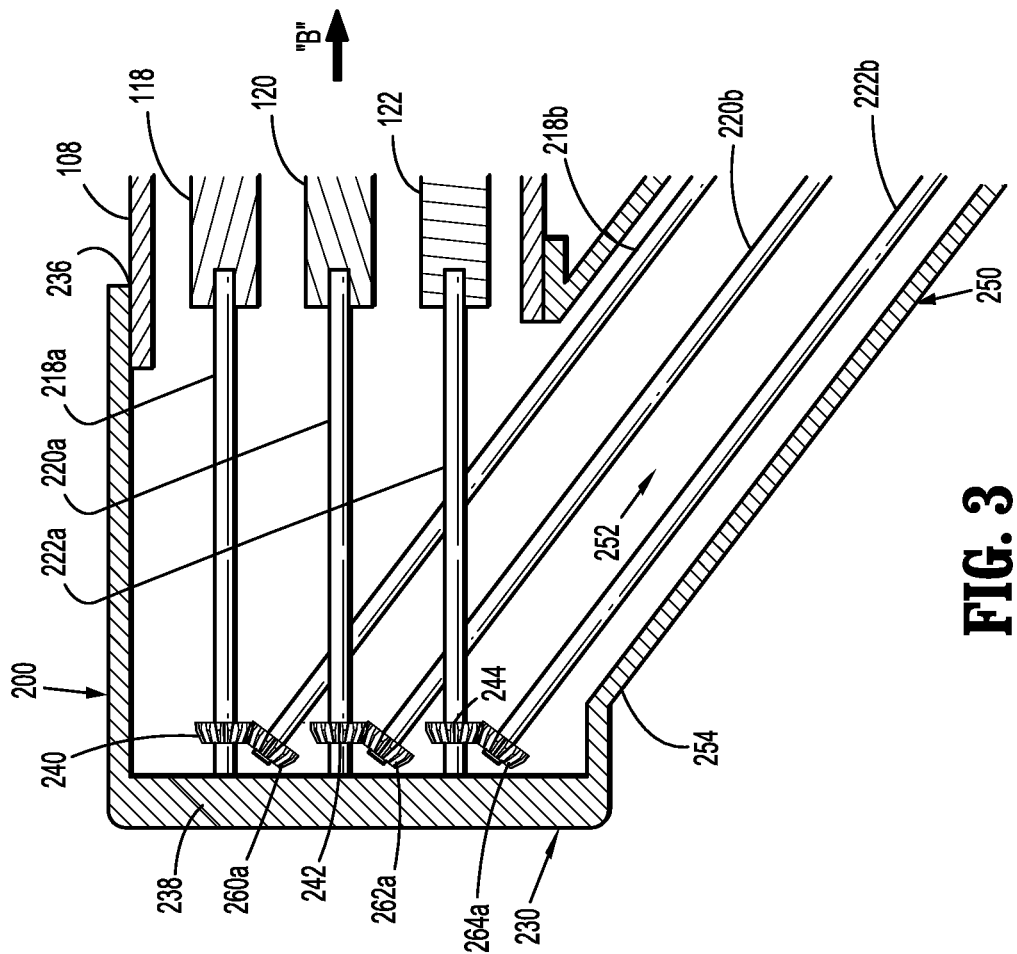
FIG. 3 is an expanded view of the indicated area of detail of FIG. 2.

As illustrated in FIGS. 1-3, handle housing 102 includes a male mating part, such as, for example, a connection portion 108 extending from distal end 112. Connection portion 108 is configured to engage a correspondingly shaped female mating part 236 of an adapter assembly 200 to connect surgical device 100 and coupling assembly 200, as will be described in greater detail below. Connection portion 108 has a substantially circular configuration. In some embodiments, connection portion 108 has alternative configurations, such as, for example, oval, non-circular, oblong, triangular, square, rectangular, hexagonal, polygonal, or star-shaped, configured for mating engagement with correspondingly shaped female mating part 236 of coupling assembly 200.

Surgical device 100 includes at least one drive shaft rotatably disposed within housing 102 for transmitting a torque from a motor of drive mechanism 122 along a pathway to surgical attachment 400. The at least one drive shaft defines a longitudinal axis "X1"-"X1" and includes three rotatable drive shafts 118, 120, 122 that extend along and from connection portion 108. Rotatable drive shafts 118, 120, 122 may be vertically and horizontally spaced from one another. In some embodiments, rotatable drive shafts 118, 120, 122 are arranged and spaced in a common plane (i.e., only vertically or horizontally spaced) with one another such that rotatable drive shafts 118, 120, 122 are aligned in a symmetrical configuration. Additionally, in the embodiment illustrated in FIGS. 2 and 3, it is contemplated that second and third drive shafts 120, 122 may be spaced an equal distance and/or opposed directions from first drive shaft 118. It is contemplated that rotatable drive shafts 118, 120, 122 may be arranged in various orientations relative to one another, such as, for example, those alternatives described herein below. In some embodiments, handle housing 102 and connection portion 108 may house fewer or more than three rotatable drive shafts.

Surgical device 100 includes a plurality of motors (not shown) disposed within handle housing 102 for driving movement of surgical attachment 400. Each motor is independently connected to one of rotatable drive shafts 118, 120, 122 so that each motor separately drives the rotation of each of rotatable drive shafts 118, 120, 122. Alternatively, surgical device 100 may include a first motor (not shown) for driving rotatable drive shafts 118, 120, 122, and a separate motor (not shown) for actuating a selection module and gear trains (not shown) for operatively engaging the first motor with a selected drive shaft 118, 120, 122.

As will be described in greater detail below, when coupling assembly 200 is mated to surgical device 100, each of rotatable drive shafts 118, 120, 122 of surgical device 100 couples with a corresponding first, second and third gear shafts 218a, 220a, 222a of coupling assembly 200, as described herein below. In this regard, the interface between corresponding first drive shaft 118 and first gear shaft 218a, the interface between corresponding second drive shaft 120 and second gear shaft 220a, and the interface between corresponding third drive shaft 122 and third gear shaft 222a are keyed to one another such that rotation of each of rotatable drive shafts 118, 120, 122 of surgical device 100 causes a corresponding rotation of the corresponding gear shafts 218a, 220a, 222a of coupling assembly 200. The mating of rotatable drive shafts 118, 120, 122 of surgical device 100 with gear shafts 218a, 220a, 222a of coupling assembly 200 allows rotational forces to be independently transmitted via each of the three respective drive shaft/gear shaft interfaces.

Distal ends of rotatable drive shafts 118, 120, 122 may each define a recess configured to matingly engage proximal ends of first, second and third gear shafts 218a, 220a, 222a of coupling assembly 200. The recesses of rotatable drive shafts 118, 120, 122 and proximal ends of gear shafts 218a, 220a, 222a may have non-circular transverse cross-sectional profiles. In some embodiments, various configurations of the recesses of the rotatable drive shafts 118, 120, 122 and the proximal ends of gear shafts 218a, 220a, 222a are contemplated, such as, for example, triangular, square, rectangular, oval, tapered, oblong, star-shaped, kidney-bean shaped, and/or polygonal. Alternatively, a coupling sleeve (not shown) may be used to interconnect distal ends of drive shafts 118, 120, 122 to corresponding proximal ends of gear shafts 218a, 220a, 222a.

Since each of rotatable drive shafts 118, 120, 122 of surgical device 100 has a keyed and/or substantially non-rotatable interface with respective gear shafts 218a, 220a, 222a of coupling assembly 200, when coupling assembly 200 is coupled to surgical device 100, rotational force(s) are selectively transferred from rotatable drive shafts 118, 120, 122 of surgical device 100 to corresponding gear shafts 218a, 220a, 222a of coupling assembly 200.

The selective rotation of rotatable drive shafts 118, 120 and/or 122 of surgical device 100 allows surgical device 100 to selectively actuate different functions of surgical attachment 400 via coupling assembly 200 and adapter assembly 300. For example, selective and independent rotation of first rotatable drive shaft 118 of surgical device 100 corresponds to the selective and independent opening and closing of tool assembly 404 (see FIG. 4) of surgical attachment 400, and driving of a stapling/cutting component of tool assembly 404 of surgical attachment 400. As an additional example, the selective and independent rotation of second rotatable drive shaft 120 of surgical device 100 corresponds to the selective and independent articulation of tool assembly 404 of surgical attachment 400 transverse to a longitudinal axis "X3"-"X3" (see FIG. 2) defined between opposite ends of adapter assembly 300. Additionally, for instance, the selective and independent rotation of third rotatable drive shaft 122 of surgical device 100 corresponds to the selective and independent rotation of surgical attachment 400 about longitudinal axis "X3"-"X3" relative to handle housing 102 of surgical device 100.

Turning to FIGS. 2 and 3, as described above, system 10 includes a coupling assembly 200 for selectively interconnecting surgical device 100 with adapter assembly 300. Coupling assembly 200 includes a first connector 230, a second connector 270 and a longitudinal element, such as, for example, an outer tube 250 disposed and connected between first and second connectors 230, 270.

As described above, first connector 230 has a cylindrical configuration and is configured for mating engagement with surgical device 100. In some embodiments, first connector 230 is variously configured, such as, for example, oval, oblong, triangular, square, hexagonal, planar, tapered, polygonal and/or undulating. First connector 230 is substantially annular and includes an inner surface 232 defining a cavity 234 or recess. Cavity 234 is in communication with a passageway 252 extending through a length of outer tube 250.

First connector 230 includes a mating part, such as, for example, female mating part 236, disposed at a proximal end thereof. Female mating part 236 is configured for mating engagement with connection portion 108 of surgical device 100, as described herein. Female mating part 236 and connection portion 108 are configured for connection in a snap fit engagement. In some embodiments, female mating part 236 and connection portion 108 are connected via alternative engagement mechanisms, such as, for example, threaded engagement, frictional engagement, lock and key engagement, latches, buttons, bayonet-type connections, welding, adhesives and/or other mechanisms. It is contemplated that coupling assembly 200 and surgical device 100 may be connected so that relative rotation is resisted and/or prevented. Female mating part 236 is oriented in a first direction, as indicated by arrow "B" in FIG. 3, facing distal end 112 or connection portion 108 of surgical device 100.

As described briefly above, first connector 230 includes a first gear shaft 218a, a second gear shaft 220a, and a third gear shaft 222a, each being disposed in cavity 234 of first connector 230. Proximal ends of gear shafts 218a, 220a, 222a are configured for connection to first, second and third rotatable drive shafts 118, 120, 122 of surgical device 100, respectively. Distal ends of gear shafts 218a, 220a, 222a are rotatably supported in or on a distal end wall 238 of first connector 230.

Gear shafts 218a, 220a, 222a include first, second and third gears 240, 242, 244, respectively, non-rotatably supported thereon. Gears 240, 242, 244 are circumferentially disposed about respective first, second and third gear shafts 218a, 220a, 222a. Gears 240, 242, 244 are configured for meshing engagement with first gears 260a, 262a, 264a of a first, second and third rotatable drive shafts 218b, 220b, 222b of coupling assembly 200, respectively, as described herein below.

Gears 240, 242, 244 can be spaced horizontally along longitudinal axis "X1"-"X1" relative to one another so that first gear 240 is disposed distal or proximal of second gear 242, and second gear 242 is disposed distal or proximal of third gear 244. In addition to gears 240, 242, 244 being spaced horizontally relative to one another, gears 240, 242, 244 may also be spaced vertically and radially relative to one another such that gears 240, 242, 244 are staggered (i.e., gears 240, 242, 244 are spaced in three dimensions) relative to one another. In some embodiments, gears 240, 242, 244 are in vertical alignment.

With continued reference to FIGS. 1-3, outer tube 250 of coupling assembly 200 extends between and has a first end 254 and a second end 256 defining a longitudinal axis "X2"-"X2" therebetween. Longitudinal axis "X2"-"X2" extends transversely, at an angle "a," relative to longitudinal axis "X1"-"X1" of surgical device 100 when coupling assembly 200 is connected to surgical device 100. First end 254 is connected to and supports first connector 230. Second end 256 is connected to and supports second connector 270. Second connector 270 defines a longitudinal axis "X3-X3" that extends transversely, at an angle "β," from longitudinal axis "X2"-"X2" of outer tube 250. In one embodiment, outer tube 250 extends at an angle less than about 90 degrees, preferably less than about 60 degrees, relative to longitudinal axis "X1"-"X1" of surgical device 100 and/or longitudinal axis "X3"-"X3" of second connector 270.

Outer tube 250 has a generally rectangular or circular configuration and a similarly shaped passageway 252 extending therethrough, defining an interior. In some embodiments, outer tube 250 and passageway 252 are variously configured, such as, for example, those alternatives described herein above and below. Outer tube 250 is monolithically and/or integrally formed with first and second connectors 230, 270. It is contemplated that outer tube 250 may be detachably engaged with first and second connectors 230, 270. Outer tube 250 is constructed from a rigid material, such as, for example, stainless steel, thermoplastic, etc.

Coupling assembly 200 includes a first, second and third rotatable drive shafts 218b, 220b, 222b disposed in passageway 252 and extending through a length of outer tube 250. First, second and third rotatable drive shafts 218b, 220b, 222b of outer tube 250 are interconnected between and in operative engagement with first, second and third gear shafts 218a, 220a, 222a of first connector 230, respectively, and a first, second, and third gear shafts 218c, 220c, 222c of second connector 270. Rotatable drive shafts 218b, 220b, 222b are substantially parallel relative to one another and spaced in a similar manner described above with regard to first, second and third gear shafts 218a, 220a, 222a of first connector 230.

First rotatable drive shaft 218b of coupling assembly 200 supports a first gear 260a that is disposed adjacent first connector 230. First gear 260a is configured for connection with first rotatable drive shaft 118 of surgical device 100 via geared engagement with first gear 240 of first gear shaft 218a. First gear 240 of first gear shaft 218a and first gear 260a of first rotatable drive shaft 218b are engaged with one another such that the transmission of torque therebetween is permitted. In some embodiments, first gear 240 of first gear shaft 218a and first gear 260a of first rotatable drive shaft 218b are variously angled relative to one another, such as, for example, obtusely, acutely, or orthogonally. First rotatable drive shaft 218b of coupling assembly 200 supports a second gear 260b that is disposed adjacent second connector 270. Second gear 260b is configured for connection with a first rotatable drive shaft 318 of adapter assembly 300 via geared engagement with a first gear 280, non-rotatably supported on a first gear shaft 218c, of second connector 270, as will be described in detail herein below.

Second rotatable drive shaft 220b of coupling assembly 200 supports first gear 262a that is disposed adjacent first connector 230, below first gear 260a of first rotatable drive shaft 218b. First gear 262a of second rotatable drive shaft 220b is configured for connection with second rotatable drive shaft 120 of surgical device 100 via geared engagement with second gear 242 of second gear shaft 220a. Second rotatable drive shaft 220b supports a second gear 262b that is disposed adjacent second connector 270, below second gear 260b of first rotatable drive shaft 218b. Second gear 262b of second rotatable drive shaft 220b is configured for connection with a second rotatable drive shaft 320 of adapter assembly 300 via geared engagement with a second gear 282, non-rotatably supported on a second gear shaft 220c, of second connector 270, as will be described in detail herein below.

Third rotatable drive shaft 222b of coupling assembly 200 supports first gear 264a that is disposed adjacent first connector 230, below first gear 262a of second rotatable drive shaft 220b. First gear 264a of third rotatable drive shaft 222b is configured for connection with third rotatable drive shaft 122 of surgical device 100 via geared engagement with third gear 244 of third gear shaft 222a. Third rotatable drive shaft 222b supports a second gear 264b that is disposed adjacent second connector 270, below second gear 262b of second rotatable drive shaft 220b. Second gear 264b of third rotatable drive shaft 222b is configured for connection with a third rotatable drive shaft 322 of adapter assembly 300 via geared engagement with a third gear 284, non-rotatably supported on third gear shaft 222c of second connector 270, as will be described in detail herein below.

In use, a rotation of first, second and third rotatable drive shafts 118, 120, 122 of surgical device 100 results in rotation of first, second and third rotatable drive shafts 318, 320, 322 of adapter assembly 300 via first, second and third rotatable drive shafts 218b, 220b, 222b of coupling assembly 200, respectively.

Second connector 270 has a cylindrical configuration and is configured for mating engagement with adapter assembly 300, which, in turn, is configured for engagement with surgical attachment 400. In some embodiments, second connector 270 is variously configured, such as, for example, oval, oblong, triangular, square, hexagonal, planar, tapered, polygonal and/or undulating. Second connector 270 is substantially annular and includes an inner surface 274 defining a cavity 276 or recess. Cavity 276 is in communication with passageway 252 of outer tube 250 such that cavities 234, 276 and passageway 252 are in communication with one another.

Second connector 270 includes a mating part 278 configured for mating engagement with a mating part 302 of adapter assembly 300. Mating parts 278, 302 are configured for connection in a snap fit engagement. In some embodiments, mating parts 278, 302 are connected via alternative engagement mechanisms, such as, for example, threaded engagement, frictional engagement, lock and key engagement, latches, buttons, bayonet-type connections, welding, adhesives and/or other mechanisms. It is contemplated that coupling assembly 200 and adapter assembly 300 may be connected so that relative rotation is resisted and/or prevented. Mating part 278 of coupling assembly 200 is oriented in a second direction, as indicated by arrow "C" in FIG. 3, facing toward adapter assembly 300 and away from surgical device 100 such that mating parts 236, 278 of first and second connectors 230, 270 are disposed on opposite sides of outer tube 250.

As described above, second connector 270 includes a first gear shaft 218c, a second gear shaft 220c, and a third gear shaft 222c, each being disposed in cavity 276. First, second and third gear shafts 218c, 220c, 222c are connectible between first, second and third rotatable drive shafts 318, 320, 322 of adapter assembly 300 and second gears 260b, 262b, 264b of first, second and third rotatable drive shafts 218b, 220b, 222b of outer tube 250, respectively. Distal ends of gear shafts 218c, 220c, 222c are configured for engagement with rotatable drive shafts 318, 320, 322 of adapter assembly 300, respectively. Proximal ends of gear shafts 218c, 220c, 222c are rotatably supported in or on a proximal end wall 272 of second connector 270. Gear shafts 218c, 220c, 222c include a first, a second and a third gear 280, 282, 284, respectively. Gears 280, 282, 284 are non-rotatably supported on respective first, second, and third gear shafts 218c, 220c, 222c, respectively. Gears 280, 282, 284 are configured for engaging second gears 260b, 262b, 264b of first, second and third rotatable drive shafts 218b, 220b, 222b of coupling assembly 200, respectively.

In some embodiments, gears 280, 282, 284 of gear shafts 218c, 220c, 222c are spaced horizontally relative to one another along longitudinal axis "X3"-"X3" so that first gear 280 is disposed proximal or distal of second gear 282, and second gear 282 is disposed proximal or distal of third gear 284. In addition to gears 280, 282, 284 being spaced horizontally relative to one another, gears 280, 282, 284 may also be spaced vertically and radially relative to one another such that gears 280, 282, 284 are staggered (i.e., gears 280, 282, 284 are spaced in three different dimensions) relative to one another. In some embodiments, gears 280, 282, 284 are non-rotatably supported about their respective gear shafts 218c, 220c, 222c in various spatial positions relative to one another. In some embodiments, gears 280, 282, 284 are aligned vertically along an axis perpendicular to longitudinal axis "X3"-"X3."

In use, female mating part 236 of first connector 230 of coupling assembly 200 is matingly engaged to connection portion 108 of upper housing portion 102a of surgical device 100. Coupling assembly 200 extends at an angle "α," such as, for example, an angle less than about 90 degrees relative to distal end 112 of upper housing portion 102a of surgical device 100 such that second connector 270 is disposed proximal of distal end 112 of upper housing portion 102a of surgical device 100 or proximal of first connector 230. In this way, surgical system 10 has a reduced overall length defined between a proximal-most end of surgical device 100 and a distal-most end of surgical attachment 400 as a result of the use of coupling assembly 200.

System 10 includes or may be used with an adapter assembly 300 for selective interconnection between surgical device 100 and surgical attachment 400, as briefly described herein above, or for selective interconnection between coupling assembly 200 and surgical attachment 400. Adapter assembly 300 includes an outer knob housing 308 and an outer tube 306 extending from a distal end of knob housing 308. Knob housing 308 and outer tube 306 are configured and dimensioned to house the components of adapter assembly 300. Outer tube 306 is dimensioned for endoscopic insertion. In particular, outer tube 306 is passable through a typical trocar port, cannula or the like. Knob housing 308 is dimensioned to not enter the trocar port, cannula or the like. Knob housing 308 is configured and adapted to connect to second connector 270 of coupling assembly 200.

Adapter assembly 300 includes first, second and third rotatable drive shafts 318, 320, 322 configured to convert a rotational force of first, second and third gear shafts 218c, 220c, 222c of second connector 270 of coupling assembly 200 into an axial force for actuating surgical attachment 400, as described herein below. Drive shafts 318, 320, 322 are arranged in a staggered configuration, similar to that described above with regard to first, second and third gear shafts 218c, 220c, 222c of second connector 270 of coupling assembly 200.

Proximal ends of rotatable drive shafts 318, 320, 322 each define a recess configured to matingly engage distal ends of first, second and third gear shafts 218c, 220c, 222c of second connector 270. The recesses of rotatable drive shafts 318, 320, 322 and distal ends of gear shafts 218c, 220c, 222c have non-circular configurations. In some embodiments, various configurations of the recesses and the distal ends of gear shafts 218c, 220c, 222c are contemplated, such as, for example, triangular, square, rectangular, oval, tapered, oblong, star-shaped, kidney-bean shaped, and/or polygonal.

Proximal ends of rotatable drive shafts 318, 320, 322 may each define a recess configured to matingly engage distal ends of first, second and third gear shafts 218c, 220c, 222c of coupling assembly 200. The recesses of rotatable drive shafts 318, 320, 322 and distal ends of gear shafts 218c, 220c, 222c may have non-circular transverse cross-sectional profiles. In some embodiments, various configurations of the recesses of the rotatable drive shafts 318, 320, 322 and the distal ends of gear shafts 218c, 220c, 222c are contemplated, such as, for example, triangular, square, rectangular, oval, tapered, oblong, star-shaped, kidney-bean shaped, and/or polygonal. Alternatively, a coupling sleeve (not shown) may be used to interconnect proximal ends of drive shafts 318, 320, 322 to corresponding distal ends of gear shafts 218c, 220c, 222c.

Each drive shaft 318, 320, 322 functions as a rotation receiving member to receive rotational forces from respective gear shafts 218c 220c, 222c of second connector 270 during actuation of motors of surgical device 100. Distal ends of rotatable drive shafts 318, 320, 322 are operatively engaged with force transmitting/converting members of adapter assembly 300 such that rotatable drive shafts 318, 320, 322 of adapter assembly 300 transmit rotational forces or convert rotational forces into axial forces for actuating surgical attachment 400.

Figure 4:
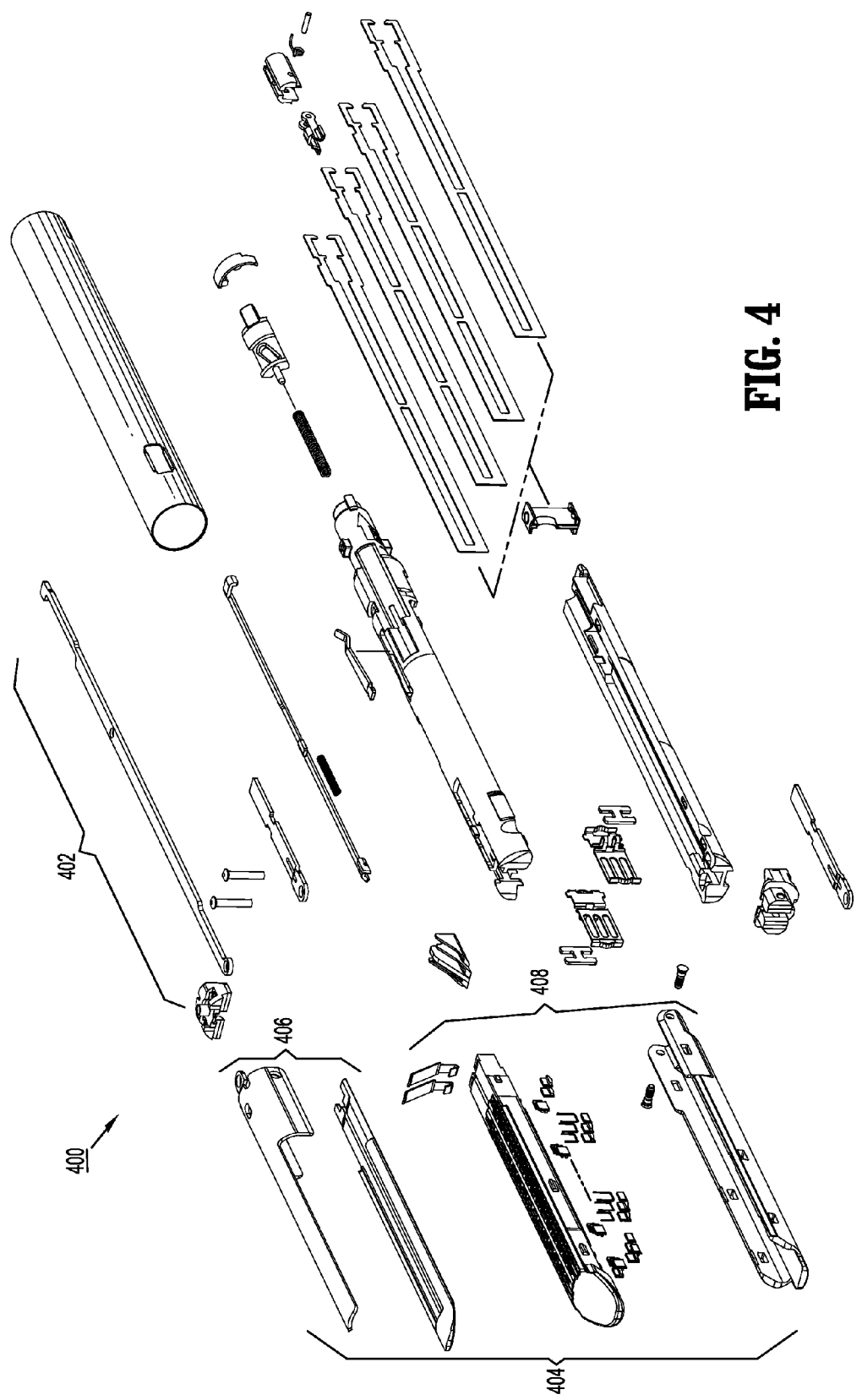
FIG. 4 is a perspective view, with parts separated, of a surgical attachment for use with the system shown in FIG. 1.

As shown in FIG. 4, system 10 further includes surgical attachment 400, which is configured for operative connection with a distal end of adapter assembly 300. In the illustrated embodiment, surgical attachment 400 extends between a proximal body portion 402 connected to outer body 306 of adapter assembly 300 and a distal tool assembly 404. Surgical attachment 400 is rotatable relative to outer body 306 about longitudinal axis "X3"-"X3." Tool assembly 404 includes a cartridge assembly 406 and an anvil assembly 408. Cartridge assembly 406 includes a stapling and cutting cartridge. Cartridge assembly 406 and anvil assembly 408 are pivotable relative to one another to clamp or unclamp material, such as, for example, tissue, therebetween.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of surgical attachment 400, as illustrated in FIG. 4.

It is contemplated that surgical attachment 400 can be something other than the surgical attachment shown in the illustrated embodiment, such as, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. Pat. No. 6,315,184; U.S. Pat. No. 6,443,973; U.S. Pat. No. 6,264,087; U.S. Pat. No. 6,348,061; U.S. Pat. No. 6,716,233; U.S. Pat. No. 6,533,157; U.S. Pat. No. 6,491,201; and U.S. Pat. No. 6,488,197; each of which is expressly incorporated herein in its entirety by reference thereto.

In assembly, operation and use, as described briefly above, female mating part 236 of first connector 230 of coupling assembly 200 is matingly engaged to connection portion 108 of upper housing portion 102a of surgical device 100. Coupling assembly 200 extends at an angle "α," such as, for example, an angle less than about 90 degrees relative to distal end 112 of upper housing portion 102a of surgical device 100 such that second connector 230 is disposed proximal to distal end 112 of upper housing portion 102a of surgical device 100.

The motors housed in surgical device 100 are selectively actuated, driving the independent rotation of first, second and third rotatable drive shafts 118, 120, 122 of surgical device 100. The rotation of first, second and third rotatable drive shafts 118, 120, 122 of surgical device 100 causes the rotation of first, second and third gear shafts 218a, 220a, 222a of first connector 230, respectively, via the keyed/non-circular interface, described herein above.

In turn, toothed outer surfaces of first, second and third gears 240, 242, 244 of first, second and third gear shafts 218a, 220a, 222a engage and drivingly rotate first gears 260a, 262a, 264a of first, second and third rotatable drive shafts 218b, 220b, 222b of outer tube 250. First, second and third rotatable drive shafts 218b, 220b, 222b of coupling assembly 200 rotate within passageway 252 of outer tube 250 to transmit torque from a first axis of rotation, such as, for example, longitudinal axis "X1"-"X1", to a second axis of rotation, such as, for example, longitudinal axis "X2"-"X2", which is angled relative to longitudinal axis "X1"-"X1."

In turn, toothed outer surfaces of second gears 260b, 262b, 264b of first, second and third rotatable drive shafts 218b, 220b, 222b of coupling assembly 200 engage and drivingly rotate first, second and third gears 280, 282, 284 of first, second and third gear shafts 218c, 220c, 222c of second connector 270. In this way, a torque that originated about longitudinal axis "X1"-"X1" is transmitted to longitudinal axis "X3"-"X3," which is radially spaced from longitudinal axis "X1"-"X1."

In turn, the rotation of first, second and third gear shafts 218c, 220c, 222c within cavity 276 of second connector 270 causes rotation of first, second and third rotatable drive shafts 318, 320, 322 of adapter assembly 300, respectively, via the keyed/non-circular interface, as described herein above. The rotation of first, second and third rotatable drive shafts 318, 320, 322 of adapter assembly 300 is either transmitted or converted to drive (i.e., rotate or translate) first, second and third drive shafts 418, 420, 422 of surgical attachment 400.

Figure 5:
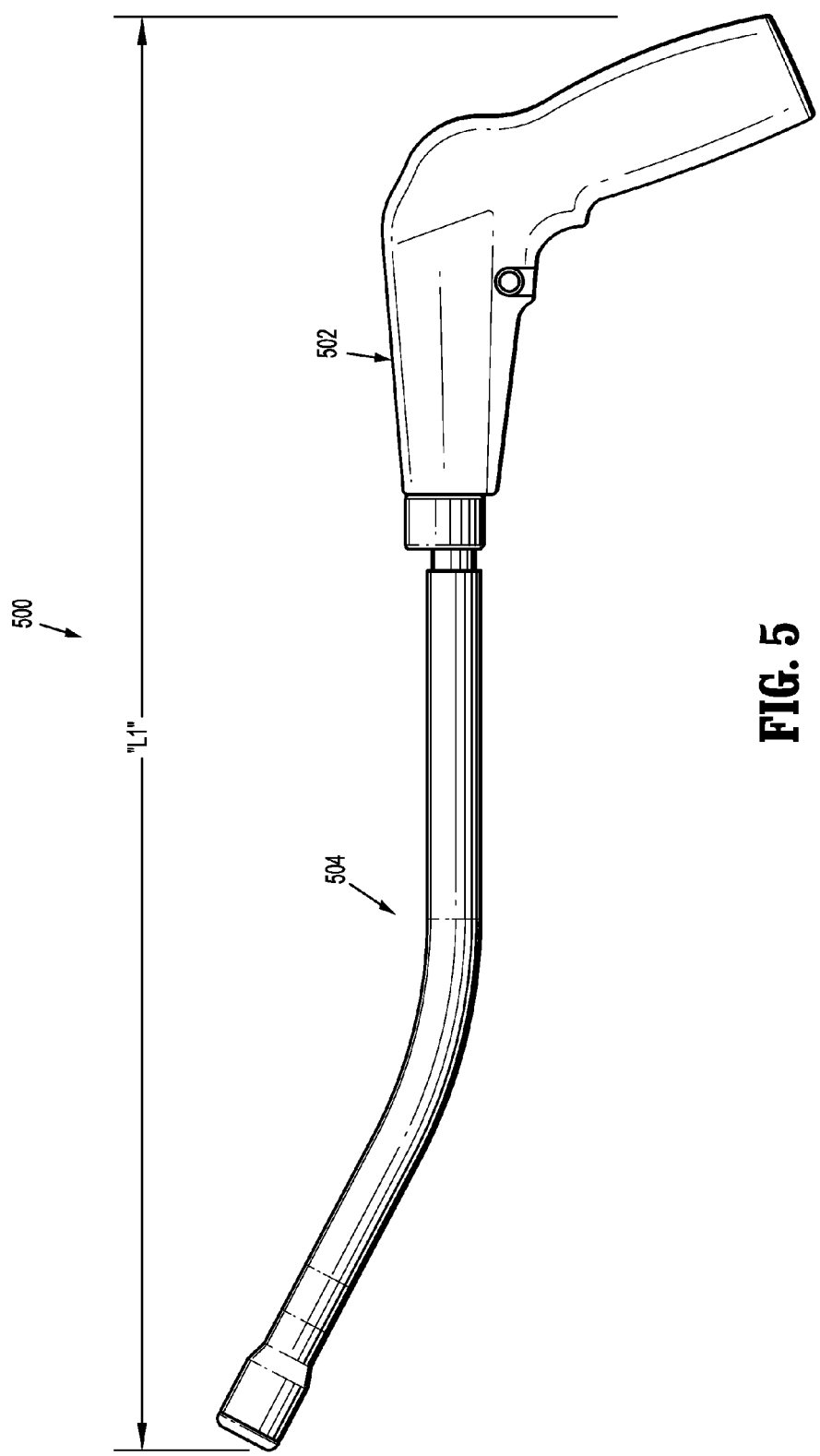
FIG. 5 is a side view of a hand-held electromechanical surgical system in accordance with the principles of the present disclosure, without a coupling member.

With reference to FIG. 5, a surgical system 500 is illustrated including a hand-held electromechanical surgical device 502, similar to surgical device 100. Surgical device 502 is connected directly to a surgical attachment, such as, for example, an adapter assembly 504, supporting an end effector, without implementing coupling assembly 200. Surgical system 500 has an overall length "L1" defined between a proximal-most end of surgical device 502 and a distal-most end of the end effector.

Figure 6:
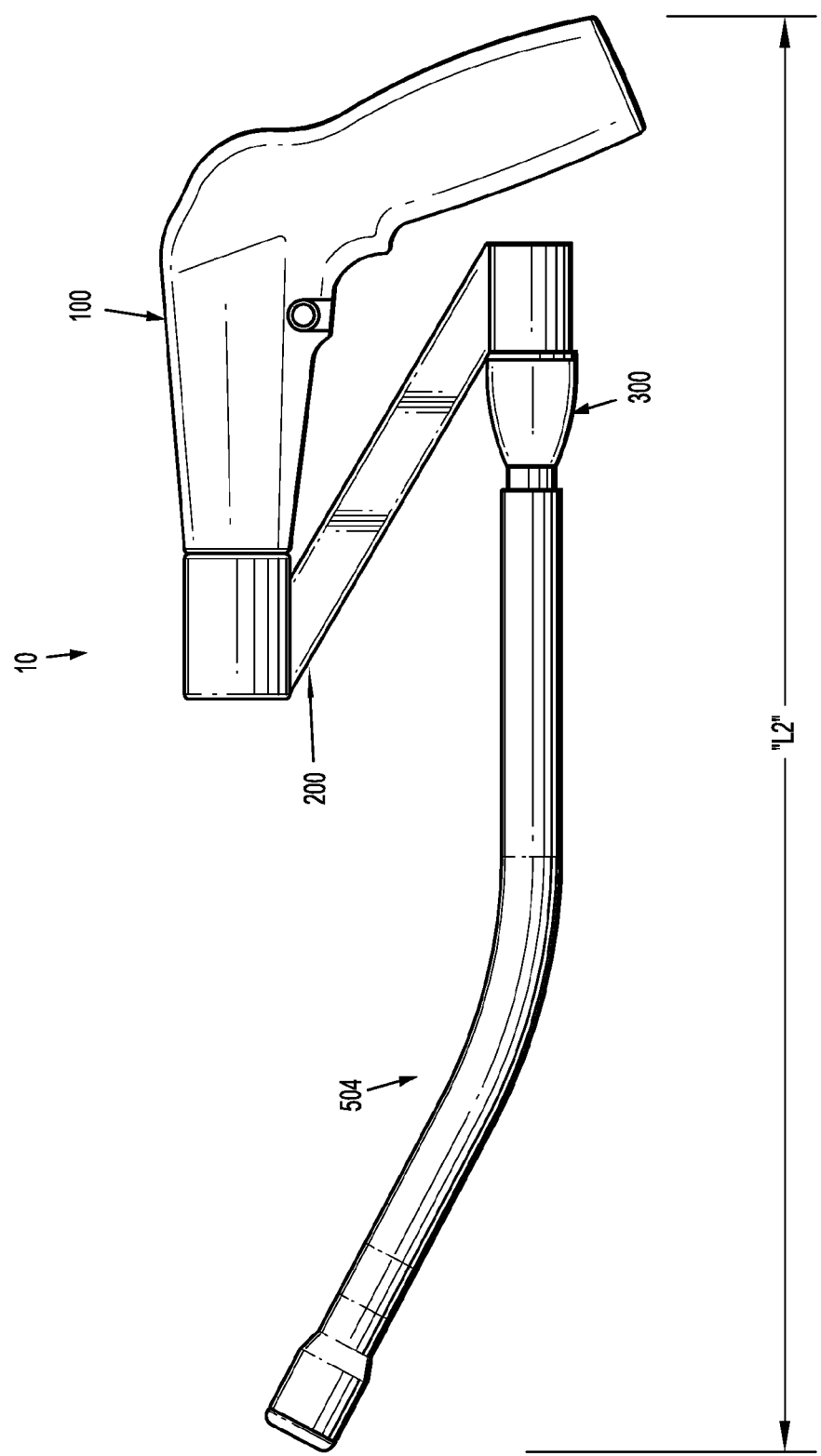
FIG. 6 is a side view of a hand-held electromechanical surgical system in accordance with the principles of the present disclosure, including the coupling member shown in FIG. 2.

With reference to FIG. 6, surgical system 10 of the present disclosure is shown, which implements coupling assembly 200. With coupling assembly 200 interconnecting adapter assembly 504 (and the end effector) with surgical device 100, surgical system 10 has an overall length "L2," which is less than length "L1" of surgical system 500. The angled configuration of coupling assembly 200 proximally shifts a position of end effector 504 relative to distal end 112 of surgical device 100. As such, coupling assembly 200 has reduced the overall length of surgical system 10 as compared to surgical system 500 and has shifted a center of gravity between the two proximally.

It is contemplated that all gears of the present disclosure may be variously configured as, such as, for example, spur gears, helical gears, miter gears, worm gears, anti-backlash gears, bevel gears, cluster gears, differential end gears, composite spur gears, and other gears known in the art.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A coupling assembly for selectively interconnecting a surgical device with an adapter assembly that is configured for connection with a surgical attachment, the coupling assembly comprising:
    a first connector configured for mating engagement with a surgical device;
    a second connector configured for mating engagement with an adapter assembly;
    an outer tube having a first end and a second end defining a longitudinal axis therebetween, the first end of the outer tube supporting the first connector and the second end of the outer tube supporting the second connector, wherein the longitudinal axis of the outer tube extends transversely relative to a longitudinal axis defined by the surgical device; and
    at least one drive shaft disposed within the outer tube, the at least one drive shaft configured to rotate relative to the outer tube to transfer rotational motion of at least one rotatable drive shaft of the surgical device to at least one rotatable drive shaft of the adapter assembly.

2. A coupling assembly as recited in claim 1, wherein the first connector is disposed distally of the second connector when the first connector is connected to the surgical device.

3. A coupling assembly as recited in claim 1, wherein the outer tube extends transversely relative to the first and second connectors.

4. A coupling assembly as recited in claim 1, wherein the at least one drive shaft of the coupling assembly supports:
    a first gear that is disposed adjacent the first connector, the first gear being configured for connection with the at least one rotatable drive shaft of the surgical device; and
    a second gear that is disposed adjacent the second connector, the second gear being configured for connection with the at least one rotatable drive shaft of the adapter assembly, wherein rotation of the at least one rotatable drive shaft of the surgical device results in rotation of the at least one rotatable drive shaft of the adapter assembly via the at least one drive shaft of the coupling assembly.

5. A coupling assembly as recited in claim 4, wherein each of the first and second connectors includes at least one gear shaft, the at least one gear shaft of the first connector is configured for connection between the at least one drive shaft of the surgical device and the first gear, and the at least one gear shaft of the second connector is configured for connection between the at least one drive shaft of the adapter assembly and the second gear.

6. A coupling assembly as recited in claim 1, wherein the first and second connectors each include an inner surface defining a cavity in communication with a passageway extending through a length of the outer tube.

7. A coupling assembly as recited in claim 1, wherein the outer tube is configured to extend at an angle less than about 90 degrees relative to the longitudinal axis of the surgical device when the coupling assembly is coupled to the surgical device.

8. A coupling assembly as recited in claim 1, wherein the outer tube is fixed relative to both the first and second connectors.

9. A coupling assembly as recited in claim 8, wherein the outer tube is monolithically formed with the first and second connectors.

10. An electromechanical surgical system, comprising:
a hand-held electromechanical surgical device configured to actuate a surgical attachment, the surgical device including:
a housing; and
at least one rotatable drive shaft supported in the housing for driving actuation of the surgical attachment, the at least one rotatable drive shaft of the surgical device defining a longitudinal axis;
an adapter assembly for selective interconnection between the surgical device and the surgical attachment, the adapter assembly including at least one rotatable drive shaft configured to transmit/convert a rotational force of the at least one rotatable drive shaft of the surgical device into an axial/rotative force for actuating the surgical attachment; and
a coupling assembly for coupling the surgical device to the adapter assembly, the coupling assembly including:
a first connector configured for mating engagement with the surgical device;
a second connector configured for mating engagement with the adapter assembly;
an outer tube having a first end and a second end defining a longitudinal axis therebetween, the first end of the outer tube supporting the first connector and the second end of the outer tube supporting the second connector, wherein the longitudinal axis of the coupling assembly extends transversely relative to the longitudinal axis of the surgical device; and
at least one drive shaft disposed within the outer tube, the at least one drive shaft of the coupling assembly being configured to rotate relative to the outer tube to transfer rotational motion of the at least one rotatable drive shaft of the surgical device to the at least one rotatable drive shaft of the adapter assembly.

11. An electromechanical surgical system as recited in claim 10, wherein the first connector is disposed distally of the second connector when the first connector is connected to the surgical device.

12. An electromechanical surgical system as recited in claim 10, wherein the outer tube extends transversely relative to the first and second connectors.

13. An electromechanical surgical system as recited in claim 10, wherein the at least one drive shaft of the coupling assembly supports:
a first gear that is disposed adjacent the first connector, the first gear being configured for connection with the at least one rotatable drive shaft of the surgical device; and
a second gear that is disposed adjacent the second connector, the second gear being configured for connection with the at least one rotatable drive shaft of the adapter assembly, wherein rotation of the at least one drive shaft of the surgical device results in rotation of the at least one rotatable drive shaft of the adapter assembly via the at least one drive shaft of the coupling assembly.

14. An electromechanical surgical system as recited in claim 13, wherein each of the first and second connectors includes at least one gear shaft, the at least one gear shaft of the first connector being configured for connection between the at least one drive shaft of the surgical device and the first gear, and the at least one gear shaft of the second connector being configured for connection between the at least one drive shaft of the adapter assembly and the second gear.

15. An electromechanical surgical system as recited in claim 10, wherein the first and second connectors each include an inner surface defining a cavity in communication with a passageway extending through a length of the outer tube.

16. An electromechanical surgical system as recited in claim 10, wherein the outer tube extends at an angle less than about 90 degrees relative to the longitudinal axis of the surgical device.

17. An electromechanical surgical system as recited in claim 10, wherein the housing includes an upper housing portion having a proximal end and a distal end and a lower hand grip portion extending from the proximal end of the upper housing portion.

18. An electromechanical surgical system as recited in claim 17, wherein the second connector is disposed proximal of the distal end of the upper housing portion when the first connector is matingly engaged with the surgical device.

19. An electromechanical surgical system as recited in claim 17, wherein the coupling assembly extends at an angle less than about 90 degrees relative to the distal end of the upper housing portion when the first connector is matingly engaged with the surgical device.

20. A coupling assembly for selectively interconnecting a surgical device with an adapter assembly that is configured for connection with a surgical attachment, the coupling assembly comprising:
a first connector configured for mating engagement with a surgical device and including at least one gear shaft configured for connection with at least one rotatable drive shaft of the surgical device;
a first gear disposed adjacent the first connector and configured for operable connection with the at least one gear shaft of the first connector;
a second connector configured for mating engagement with an adapter assembly and including at least one gear shaft configured for connection with at least one rotatable drive shaft of an adapter assembly;
a second gear disposed adjacent the second connector and configured for operable connection with the at least one gear shaft of the second connector;
an outer tube having a first end and a second end defining a longitudinal axis therebetween, the first end of the outer tube supporting the first connector and the second end of the outer tube supporting the second connector, wherein the longitudinal axis of the outer tube extends transversely relative to a longitudinal axis defined by the surgical device; and
at least one rotatable drive shaft disposed within the outer tube, the at least one rotatable drive shaft of the coupling assembly supporting the first and second gears such that rotation of the at least one rotatable drive shaft of the surgical device results in rotation of the at least one rotatable drive shaft of the adapter assembly via the at least one rotatable drive shaft of the coupling assembly.

* * * * *